(12) United States Patent
Johnson

(10) Patent No.: US 10,639,391 B2
(45) Date of Patent: May 5, 2020

(54) RE-PHRESH SYSTEM

(71) Applicant: Allanna Shakira Johnson, Chicago, IL (US)

(72) Inventor: Allanna Shakira Johnson, Chicago, IL (US)

(*) Notice: Subject to any disclaimer, the term of this patent is extended or adjusted under 35 U.S.C. 154(b) by 0 days.

(21) Appl. No.: 15/390,653

(22) Filed: Dec. 26, 2016

(65) Prior Publication Data

US 2019/0125910 A1 May 2, 2019

(51) Int. Cl.
| | |
|---|---|
| A61L 2/26 | (2006.01) |
| A61L 2/18 | (2006.01) |
| A47L 25/00 | (2006.01) |
| B08B 1/00 | (2006.01) |
| B08B 1/04 | (2006.01) |
| B08B 3/08 | (2006.01) |
| A46B 13/00 | (2006.01) |
| A46B 13/04 | (2006.01) |
| A46B 9/02 | (2006.01) |
| E03D 9/00 | (2006.01) |

(52) U.S. Cl.
CPC ............ *A61L 2/26* (2013.01); *A46B 9/026* (2013.01); *A46B 13/001* (2013.01); *A46B 13/04* (2013.01); *A47L 25/00* (2013.01); *A61L 2/18* (2013.01); *B08B 1/002* (2013.01); *B08B 1/04* (2013.01); *B08B 3/08* (2013.01); *E03D 9/00* (2013.01); *A46B 2200/3033* (2013.01); *A61L 2202/121* (2013.01); *A61L 2202/17* (2013.01)

(58) Field of Classification Search
CPC .............. A61L 2/18; A61L 2/26; A47L 25/00
See application file for complete search history.

(56) References Cited

U.S. PATENT DOCUMENTS

| | | | | |
|---|---|---|---|---|
| 5,836,322 A | * | 11/1998 | Borger | A47K 11/10 134/42 |
| 6,383,457 B1 | * | 5/2002 | Brown | A61L 2/18 134/42 |
| D471,393 S | * | 3/2003 | Hutchinson | D6/551 |
| 7,841,029 B1 | * | 11/2010 | Williams | E03D 9/06 4/661 |
| 9,464,424 B1 | * | 10/2016 | Wiltshire | E03D 9/005 |
| 2006/0213791 A1 | * | 9/2006 | Holden | A47K 17/00 206/349 |
| 2011/0253180 A1 | * | 10/2011 | Davidson | A46B 17/06 134/135 |

* cited by examiner

Primary Examiner — Sean E Conley

(57) ABSTRACT

A convenient way to sanitize a toilet plunger after it has been used to prevent the spreading of germs and bacteria around the bathroom. This device will be used to immerse the used plunger in a sanitizing solution, before it is stored.

1 Claim, 3 Drawing Sheets

RE-PHRESH SYSTEM

BACKGROUND OF THE INVENTION

1. Field of the Invention

The present invention relates generally to the field of sanitizing devices and more specifically relates to a convenient way to sanitize a toilet plunger after it has been used to prevent the spreading of germs and bacteria around the bathroom. This device will be used to immerse the used plunger in a sanitizing solution, before it is stored.

2. Description of the Related Art

Bacteria and germs thrive in dark damp places, causing bathrooms to be fertile grounds for spreading bacteria and germs. They can create unpleasant odors as well as unsanitary conditions for all who have to use them. In most households, toilet bowl brushes are needed to keep toilets clean and sanitary, and often a plunger may be needed to unstop a toilet, especially when the fixtures and plumbing are old. These items should be kept in a convenient place, usually next to the toilet or in a cabinet nearby, so they are accessible when needed. Since plungers are used in toilets, they are extra smelly and unsanitary, and people worry about children touching them. Therefore a need exists for a way to sanitize bathroom plungers, which will be more affordable than replacing them after each use.

Various attempts have been made to solve the problems which may be found in the related art but have thus far been unsuccessful. A need exists for a reliable Re-Phresh System to avoid the above-mentioned problems.

BRIEF SUMMARY OF THE INVENTION

In view of the foregoing disadvantages inherent in the known art, the present invention provides a novel Re-Phresh System. The general purpose of the present invention, which will be described subsequently in greater detail, is to provide a convenient way to sanitize a toilet plunger after it has been used to prevent the spreading of germs and bacteria around the bathroom. This device will be used to immerse the used plunger in a sanitizing solution, before it is stored. This device will be used to immerse the used plunger in a sanitizing solution, before it is stored. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, Re-Phresh System, constructed and operative according to the teachings of the present invention.

The various embodiments of the present invention will hereinafter be described in conjunction with the appended drawings.

DETAILED DESCRIPTION

As discussed above, embodiments of the present invention relate to a sanitizing device and more particularly to a Re-Phresh System.

Figure 1:
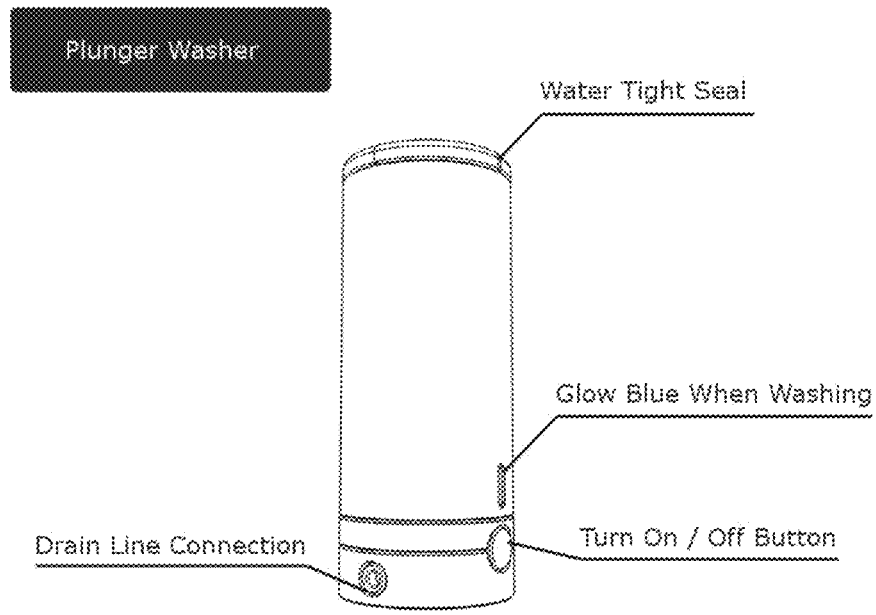
FIGS. 1-5 show various perspective views illustrating Re-Phresh System according to an embodiment of the present invention.
Figure 2:
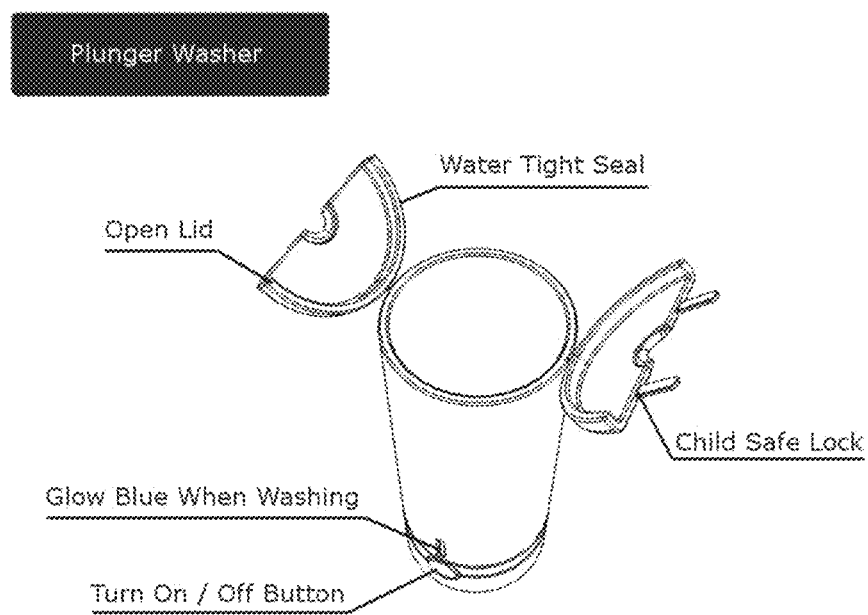
Figure 3:
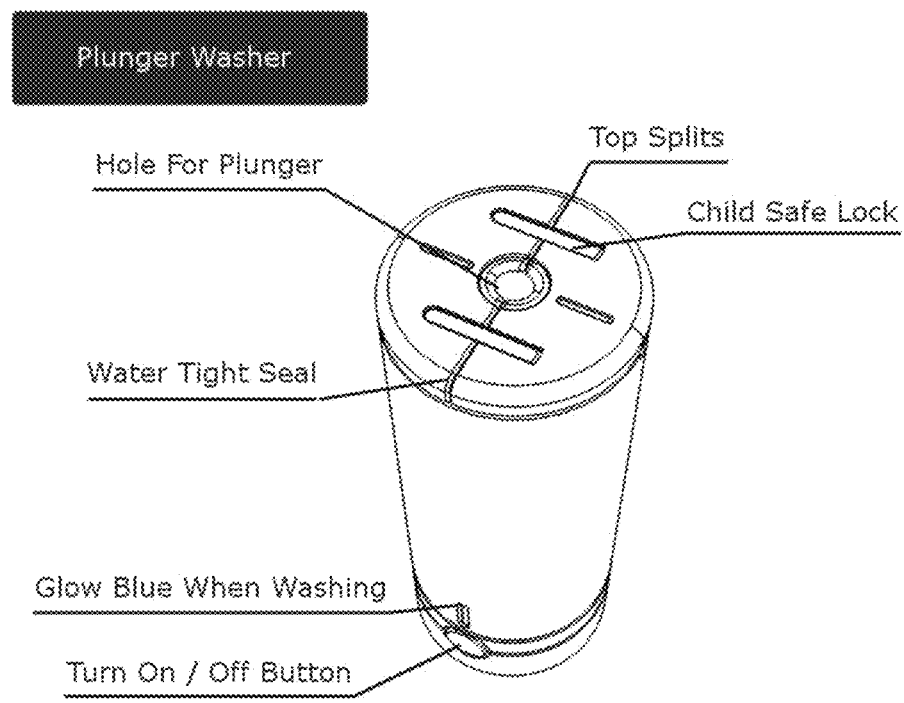
Figure 4:
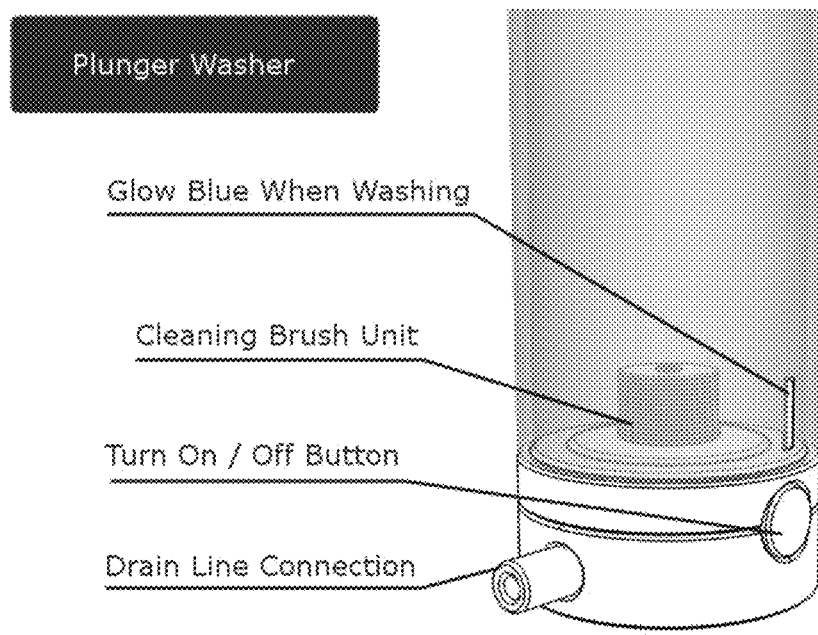
Figure 5:
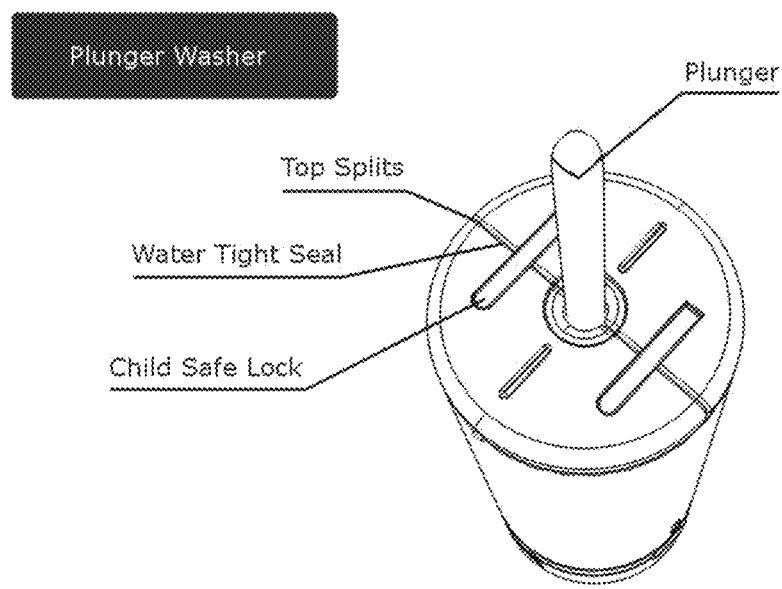

Referring now to the drawings FIGS. 1-5, the Re-Phresh System for sanitizing plungers can be kept beside the toilet or in a nearby cabinet to provide convenient storage for plungers. The top of the unit splits open to allow the used plunger to be inserted. The rubber part of the plunger rests on the bottom, and the unit is tall enough to sanitize the handle, which has been exposed to germ-infested water, as well. There are two internal compartments, one for water and the other for a sanitizing solution. The top closes around the handle, creating a water-tight seal, and the device is turned on by pressing the power button. A green light on the front indicates is working, and a red light means it has stopped or is ready to be used again.

The user can also select if they would like to rinse the plunger a second time by pressing a switch to make that selection. There is a retractable hose that allows the used water and sanitizing solution to be dumped into the toilet after the plunger has been washed. When not in use, the hose tucks inside the machine and is secured with a child safety lock. The water and cleaning solution is released, and the internal brushes are activated to scrub away the bacteria, feces, urine, etc., from the plunger and its handle. The machine will beep when it is finished washing the plunger, and unit can be unlocked to allow air to circulate and dry the clean plunger, to prevent the development of mildew. It is designed to fit all styles of toilet bowl plungers. Future versions can be designed to clean toilet bowl brushes as well.

The unique features of this invention will provide the following benefits for consumers everywhere:
  A convenient, hands-free way to sanitize a plunger after it has been used to unstop a toilet
  Will eliminate germs and bacteria that accumulate on plungers and will eliminate the need to discard the plunger after it has been used
  Can be used to provide convenient storage for a plunger, without owners worrying about the potential for germs and bacteria to spread around the bathroom
  The water, sanitizing solution, and debris will be flushed away, down the toilet The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Allana Johnson is set forth in the appended claim:

1. A device for sanitizing toilet plungers, the device comprising:
   a cylindrical housing sized for holding a toilet plunger; wherein said toilet plunger has a plunger head and handle;
   a lid attached to the top of the cylindrical housing for forming a water tight seal at the top of said cylindrical housing, said lid being formed of two parts, said two parts being a first half and a second half, wherein said first half and said second half are each attached to the top of cylindrical housing, the first half and the second half meeting at the middle of the opening in the top of the cylindrical housing to form a closed lid and creating a water tight seal on the top of the cylindrical housing and around said handle of the toilet plunger, thereby preventing water from escaping from the top of the device;

a child safety lock attached to the lid for securing the lid in a locked closed position during use;

a first compartment containing water and a second compartment containing sanitizing solution, said first compartment and said second compartment being located within said cylindrical housing; and a power button located on the exterior of the cylindrical housing for activating a washing/sanitizing cycle, said power button includes indicator lights to display to the user that the device is operating;

a timer electrically connected to a water pump for controlling the duration of time that the water pump is activated during a washing/sanitizing cycle;

at least one brush located inside the cylindrical housing for scrubbing away bacteria, feces, and urine from the plunger head and handle when the at least one brush is activated by the user;

a retractable hose that allows used water and sanitizing solution to be dispensed into the toilet after said toilet plunger has been washed and sanitized, said retractable hose being tucked inside said device and secured with a lock when not in use; and a plurality of cleaning head attachments to accommodate different size plungers.

\* \* \* \* \*